United States Patent
Wood

(10) Patent No.: US 7,504,252 B2
(45) Date of Patent: Mar. 17, 2009

(54) APPARATUS AND METHODS FOR SCANNING AND PRODUCING BIOLOGICAL SPECIMEN FILM STRIPS

(75) Inventor: Nathan P. Wood, Winchendon, MA (US)

(73) Assignee: Cytyc Corporation, Marlborough, MA (US)

( * ) Notice: Subject to any disclaimer, the term of this patent is extended or adjusted under 35 U.S.C. 154(b) by 633 days.

(21) Appl. No.: 10/867,605

(22) Filed: Jun. 14, 2004

(65) Prior Publication Data

US 2005/0277168 A1    Dec. 15, 2005

(51) Int. Cl.
*C12M 1/34* (2006.01)
*C12M 3/00* (2006.01)

(52) U.S. Cl. ............... 435/287.3; 435/3; 435/288.7
(58) Field of Classification Search .............. 435/287.3, 435/3, 288.7; 422/66, 73
See application file for complete search history.

(56) References Cited

U.S. PATENT DOCUMENTS

| | | | | |
|---|---|---|---|---|
| 3,493,447 A | * | 2/1970 | Rock et al. ............... | 156/57 |
| 3,941,981 A | * | 3/1976 | Abe et al. ............... | 377/18 |
| 3,979,264 A | * | 9/1976 | Buerger .................. | 435/34 |
| 4,071,315 A | * | 1/1978 | Chateau ................. | 436/518 |
| 4,146,414 A | * | 3/1979 | Stormby ................. | 156/57 |
| 4,883,642 A | * | 11/1989 | Bisconte ................. | 422/66 |
| 5,092,466 A | * | 3/1992 | Anderson ............... | 206/438 |
| 5,632,376 A | * | 5/1997 | Ozeki .................... | 206/456 |
| 6,112,031 A | * | 8/2000 | Stephenson ............. | 396/308 |
| 6,362,004 B1 | * | 3/2002 | Noblett ................... | 436/43 |
| 6,878,345 B1 | * | 4/2005 | Astle .................... | 422/102 |
| 7,006,674 B1 | * | 2/2006 | Zahniser et al. ........... | 382/128 |
| 2004/0151637 A1 | * | 8/2004 | Davin ................... | 422/102 |

OTHER PUBLICATIONS

Schildkraut E.R., Herche M., Shapiro H.M., Young R.E., Matsu N., Brown D.C. and Webb R.H. A System for Storage and Retrieval of Individual Cells Following Flow Cytometry.1979. The Journal of Histochemistry and Cytochemistry.vol. 27, No. 1,pp. 289-292.*

* cited by examiner

*Primary Examiner*—Walter D Griffin
*Assistant Examiner*—Shanta G Doe
(74) *Attorney, Agent, or Firm*—Vista IP Law Group, LLP

(57) ABSTRACT

A biological specimen film reel, a biological specimen film assembler, and a biological specimen scanner are provided. The biological specimen film reel comprises a reel carrying a film having a plurality of biological specimens disposed thereon. The biological specimen film assembler comprises a film manipulator and a specimen transfer device. The biological specimen scanner comprises a film manipulator for mechanically manipulating a strip of flexible film with a plurality of biological specimens affixed thereto and a scanning device. Methods for preparing and analyzing the biological specimen film are also provided.

30 Claims, 8 Drawing Sheets

APPARATUS AND METHODS FOR SCANNING AND PRODUCING BIOLOGICAL SPECIMEN FILM STRIPS

FIELD OF THE INVENTION

The present inventions generally relate to devices and methods for preparing and analyzing biological specimens, and more particularly to automated or semi-automated devices and methods for preparing and analyzing biological specimens.

BACKGROUND OF THE INVENTION

In the medical industry, there is often a need for a laboratory technician, e.g., a cytotechnologist, to review a cytological specimen for the presence of specified cell types. For example, there is presently a need to review a cervico-vaginal Papanicolaou (Pap) smear slides for the presence of malignant or pre-malignant cells. Since its introduction over fifty years ago, Pap smears have been a powerful tool for detecting cancerous and precancerous cervical lesions. During that time, the Pap smear has been credited with reducing mortality from cervical cancer by as much as 70%. This once precipitous drop in the death rate has slowed however, and the mortality rate in the United States for this preventable disease has remained virtually constant, at about 5,000 per year since the mid-eighties. Therefore, about one-third of the 15,000 women diagnosed with cervical cancer annually still die, because the cancer was detected too late. A further cause for concern is National Cancer Institute data that shows an annual 3% increase in the incidence of invasive cervical cancer in white women under 50 years of age since 1986.

A number of factors may be contributing to this current threshold, not the least of which is the fact that many women, particularly in high risk populations, are still not participating in routine cervical cancer screening. Another contributing factor that has received much attention is the limitation of the traditional Pap smear method itself.

The reliability and efficacy of a cervical screening method is measured by its ability to diagnose precancerous lesions (sensitivity) while at the same time avoiding false positive diagnosis (specificity). In turn, these criteria are dependent on the accuracy of the cytological interpretation. The conventional Pap smear has false negative rates ranging from 10-50%. This is due in large part to the vast number of cells and objects (typically as many as 100,000 to 200,000) that must be reviewed by a technician to determine the possible existence of a small number of malignant or pre-malignant cells. Thus, Pap smear tests, as well as other tests requiring detailed review of biological material, have suffered from a high false negative rate due to fatigue imposed on the technician.

To facilitate this review process, automated biological screening (ABS) systems have been developed to focus the cytotechnologist's attention on the most pertinent cells, with a potential to discard the remaining cells from further review. A typical ABS system includes an imager, processor and automated viewing microscope. The imager acquires a series of images of a specimen slide, each image depicting a different portion of the slide. The processor then processes these images to identify the most pertinent biological objects for subsequent viewing by a technician, and their locations (x-y coordinates) in the frame. This information is then passed onto the microscope, which automatically proceeds to the x-y coordinates and centers on the biological objects for review by the technician. Alternatively, images of suspicious biological objects may be presented for viewing on a monitor.

The robotics used in ABS systems to handle and place large volumes of sample slides is bulky, complicated, and expensive. Also, the slide cassettes needed to store a large volume of sample slides are bulky and make archiving sample slides a costly endeavor. Accordingly, there remains a need for a more simple and less expensive device and method for handling and storing large volumes of biological samples.

SUMMARY OF THE INVENTION

In accordance with a first aspect of the present inventions, a biological specimen film is provided. The specimen film comprises a strip of film, film advancers located along the film strip to facilitate advancement of the film, and a plurality of biological specimens disposed along the film strip. In one embodiment, the biological specimens are cytological specimens, such as those taken from a cervix. The biological specimens, however, can alternatively be tissue or viral samples. The number of biological specimens affixed along the film strip can be any plural number, but in one embodiment, the number of specimens is at least 200 in order to minimize user intervention. In one embodiment, the specimens are disposed along the film strip in a single column, but can alternatively be disposed along the film strip in multiple columns as well. In one embodiment, a plurality of slides is disposed along the film strip and the biological specimens are affixed to the slides. In another embodiment, the biological specimens are affixed directly onto the film strip. The specimen film may optionally comprise a plurality of discrete affixation covers disposed along the film strip over the specimens.

In one embodiment, the specimen film may comprise at least one fiducial mark located on the film strip adjacent each biological specimen. The fiducial marks can be used, e.g., to establish coordinate systems for the biological specimens. The specimen film may also comprise identifiers located on the film strip. Such identifiers contain unique information on the respective biological specimens. The specimen film may also comprise a counter mark located on the film strip adjacent each biological specimen. In this manner, the count of a particular biological specimen can be determined.

In accordance with a second aspect of the present inventions, a biological specimen film reel is provided. The film reel comprises a strip of film, a plurality of biological specimens affixed on the film strip, and a reel carrying the film strip. The biological specimens can, e.g., be cytological specimens, or alternatively, tissue or viral specimens, and can be applied to the film strip as a single column or multiple columns in any plurality number, e.g., 200 or more. Discrete affixation covers can be applied to the film strip over the respective specimens. The film reel may optionally comprise fiducial marks, identifiers, counter marks, film advancers as previously described herein. The use of a reel to carry the film strip provides a convenient means for storing and scanning the biological specimens.

In accordance with a third aspect of the present inventions, a method of preparing biological specimens is provided. The method comprises providing a film strip, and applying a plurality of biological specimens along the film strip. The biological specimens can, e.g., be cytological specimens, or alternatively, tissue or viral specimens, and can be applied to the film strip as a single column or multiple columns in any plurality number, e.g., 200 or more. Discrete affixation covers can be applied to the film strip over the respective specimens. In one method, the biological specimens are automatically applied to the film, but can alternatively, be applied manually to the film as well. One method comprises winding the film strip around a reel to facilitate storage and scanning of the biological specimens. The film strip may optionally comprise fiducial marks and/or counter marks, in which case, each biological specimen can be applied adjacent a corresponding fiducial mark and/or counter mark. The method may optionally comprise applying identifiers and/or film advancers along the length of the film strip.

In accordance with a fourth aspect of the present inventions, a biological specimen film assembler is provided. The assembler comprises a film manipulator for mechanically manipulating a strip of film, and a specimen transfer device for disposing a plurality of biological specimens on the film strip. In one embodiment, the film manipulator comprises a dispensing reel holder for holding a dispensing reel that dispenses the film strip to the specimen transfer device, and a take-up reel holder for holding a take-up reel that collects the film strip from the specimen transfer device. The film manipulator may also comprise an advancing device for operably engaging film advancers located on the film strip to advance the film strip. In one embodiment, the film manipulator is automated to minimize user intervention, but may also be manually operated as well.

The specimen transfer device can be automated or manual and can take the form of any device that can apply biological specimens to a surface. In one embodiment, the specimen transfer device comprises a specimen transfer filter and a pneumatic source for applying a vacuum to the filter. The assembler may optionally comprise a laminating device for applying a discrete affixation cover onto the film strip over each biological specimen, a printer for printing the previously described specimen identifiers on the film strip, and a counting device for operably engaging counter marks on the film strip to count the biological specimens.

In accordance with a fifth aspect of the present inventions, a method of scanning biological specimens is provided. The method comprises providing a strip of film with a plurality of biological specimens disposed thereon, and scanning the biological specimens on the film strip, which can then be optionally analyzed. The biological specimens may, e.g., be cytological specimens, or alternatively, tissue or viral specimens. The scanning may comprise acquiring images of the biological specimens and/or magnifying the biological specimens.

One method may comprise advancing the film strip by dispensing the film from a dispensing reel and collecting the film onto a take-up reel. The method may optionally comprise establish a coordinate system for each biological specimen, e.g., by using fiducial marks printed next to the specimens. The method may also optionally comprise electronically reading unique indicia for each biological specimen, e.g., by using specimen identifiers printed next to the specimens. The method may optionally comprise counting the biological specimens.

In accordance with a sixth aspect of the present invention, a biological specimen scanner is provided. The scanner comprises a film manipulator for mechanically manipulating a strip of film having biological specimens affixed thereon, a scanning device for scanning the biological specimens on the film strip, and an optional analyzer for analyzing the scanned biological specimens. In one embodiment, the film manipulator comprises a dispensing reel holder for holding a dispensing reel that dispenses the film strip to the scanning device, and a take-up reel holder for holding a take-up reel that collects the film strip from the scanning device. The film manipulator may also comprise an advancing device for operably engaging film advancers located on the film strip to advance the film strip. In one embodiment, the film manipulator is automated to minimize user intervention, but may also be manually operated as well.

In one embodiment, the scanning device comprises a camera, such as a CCD camera, for acquiring images of the biological specimens. In another or the same embodiment, the scanning device may comprise a microscope for magnifying the biological specimens, e.g., to provide magnified images of the biological specimens and/or to allow a user to directly view the biological specimens.

The scanner may optionally comprise an indexer for reading fiducial marks located on the film adjacent the biological specimens and indexing the scanning device to the biological specimens. The scanner may further optionally comprise an electronic reader for reading specimen identifiers located on the film strip and/or a counting device for operably engaging counter marks located on the film strip adjacent the biological specimens to count the biological specimens.

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which.

DETAILED DESCRIPTION OF THE PREFERRED EMBODIMENTS

Figure 1:
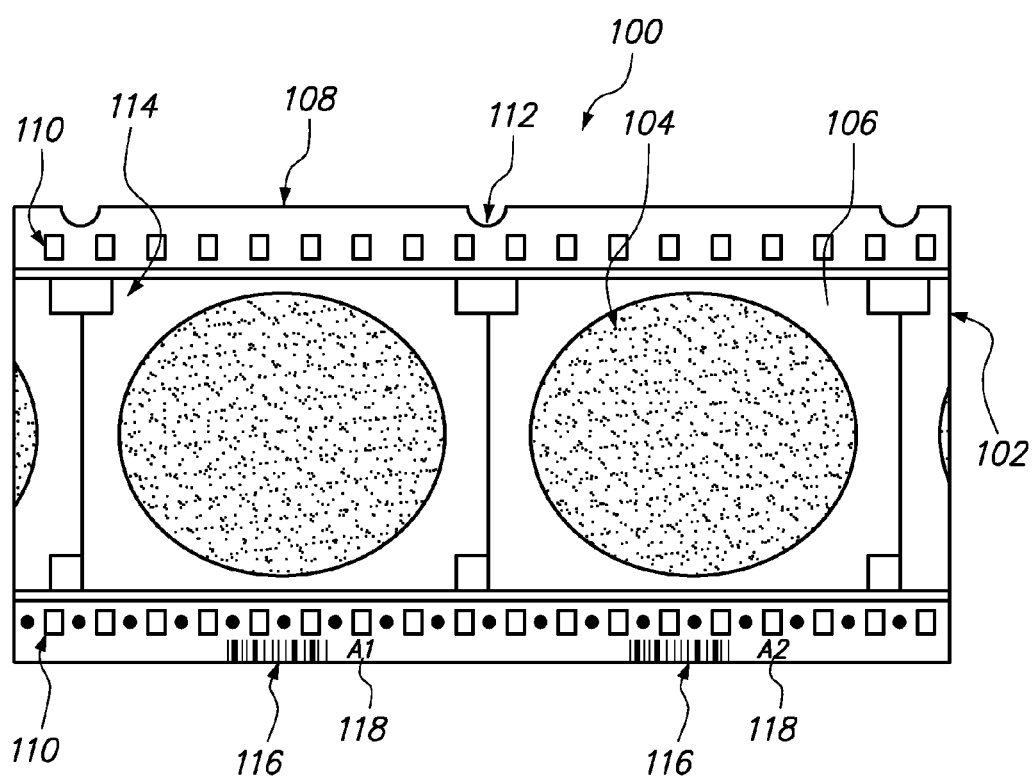
FIG. 1 is a top view of a biological specimen film constructed in accordance with a preferred embodiment of the present invention.

Referring to FIG. 1, a preferred embodiment of a biological specimen film 100 will now be described. The specimen film 100 generally comprises a narrow film strip 102, a plurality of biological specimens 104 disposed on the film strip 102, and affixation covers 106 mounted to the film strip 102 over the biological specimens 104.

The film strip 102 is topologically divided into a plurality of discrete biological specimen frames 108, such that each biological specimen 104 and its corresponding affixation cover 106 is contained in one specimen frame 108. The film strip 102 can be manufactured from any non-stretchable, flexible, transparent material on which biological material can be adhered, such as cellulose triacetate and vinyl. In the illustrated embodiment, the biological specimens 104 are cytological specimens taken from, e.g., the cervix. Alternatively, the biological specimens 104 may take the form of tissue specimens, or even viral specimens. The discrete covers 106 are adhered onto the film strip 102 over each biological specimen 104, such that each biological specimen 104 is encased between the film strip 102 and the respective cover 106. In the illustrated embodiment, a bonding agent, which is preferably transparent and non-distorting is used to adhere the discrete covers 106 to the film strip 102. Alternatively, the discrete covers 106 can be laminated onto the film strip 102. Alternatively, instead of using discrete covers 106, another film strip (not shown) can be adhered onto the film strip 102 over the biological specimens 102. The use of discrete covers 106, however, allows the specimen film 100 to be conveniently wound onto a biological film reel while minimizing wrinkling of the specimen film 100.

The film 100 further comprises advancers 110 that take the form of two lines of holes that extend along the two respective longitudinal edges of the film strip 102. As will be described in further detail below, these advancers 110 can be engaged with a rotating cog in order to advance or rewind the film 100. The film 100 also comprises counter marks 112 that take the form of notches cut into one of the longitudinal edges of the film strip 102. In the illustrated embodiment, each counter mark 112 is located between adjacent frames 108, thereby allowing the number of biological specimens 104 to be counted, as will be described in further detail below.

The specimen film 100 also comprises three fiducial marks 114 printed in each specimen frame 108 using a suitable process, such as silk screening. In the illustrated embodiment, each set of fiducial marks 114 is arranged in a non-collinear relationship and in the same positions in each frame 108. The fiducial marks 114 are visible in a field of view of an optical instrument, such as a microscope or a camera, and can be used as a reference datum to establish a coordinate system in the respective specimen frame 108 or for measurement calibration purposes. In the illustrated embodiment, the fiducial marks 114, each have a diameter of about 0.010 inches and have a location tolerance of about +/−0.015 inches. The fiducial marks 114 may optionally have sharp edges to facilitate focusing of a microscope, as will be described in further detail below.

The specimen film 100 further comprises sample identification marks in the form of machine-readable indicia 116 and human-readable indicia 118, which are applied to the film strip in a suitable manner, such as printing. The machine-readable indicia 116 contain information necessary for matching the results of an analysis with the correct patient; for example, identification of the patient from whom the biological specimen 104 in the specimen frame 108 was obtained, or the doctor that provided the biological specimen 104. In the illustrated embodiment, the machine-readable indicia 116 take the form of a barcode, and the human-readable indicia 118 take the form of alphanumeric characters. The use of both machine-readable indicia 116 and human-readable indicia 118 allows a machine, such as a scanner, to more easily process the specimens 104, while allowing a cytologist to visually identify the specimens 104. Because biological specimens are often archived and retained for extended periods, it is generally desirable to avoid using an indicia standard that may fall into disuse or become obsolete. It is also generally desirable that the reels also have indicia of their own to facilitate references to a particular specimen 104 on a particular reel.

Figure 2:
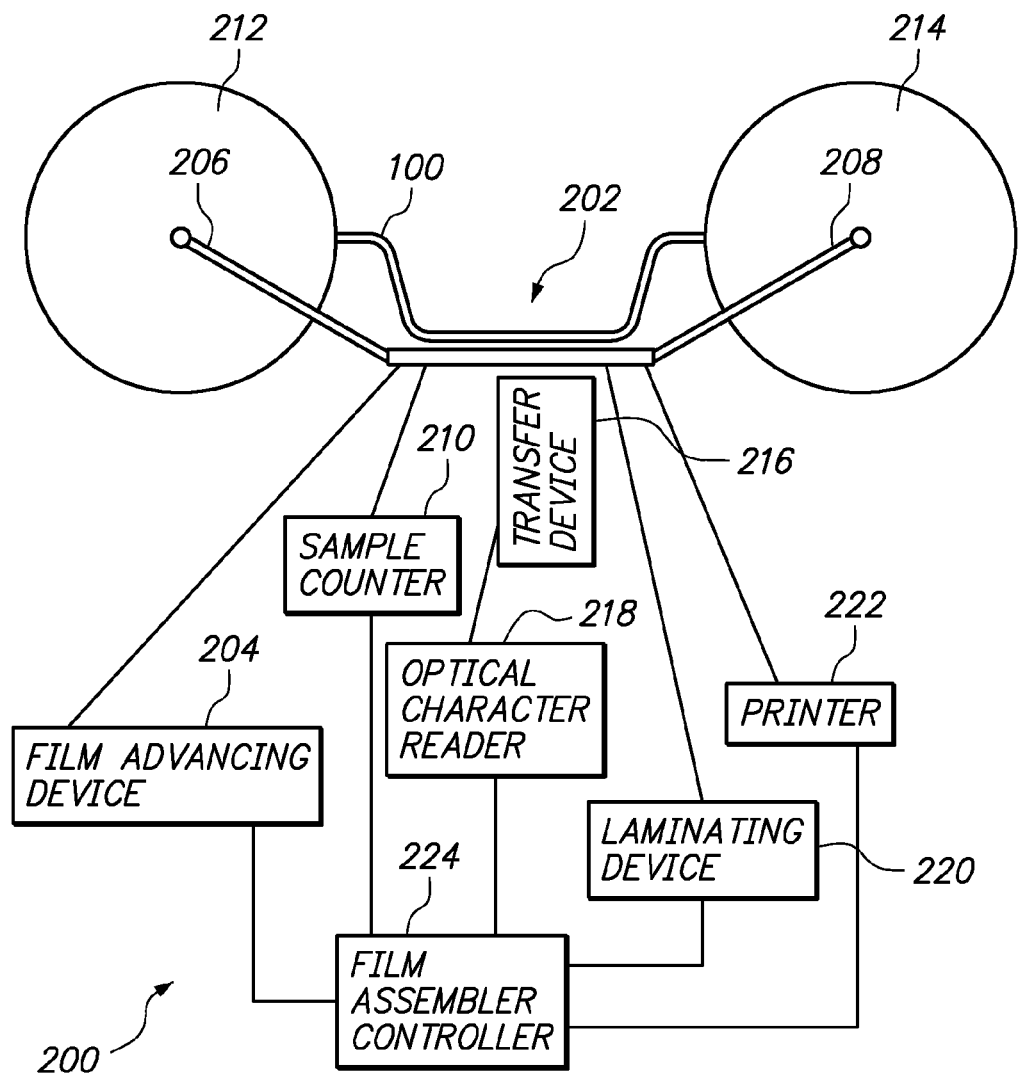
FIG. 2 is a schematic diagram of a biological specimen film assembler constructed in accordance with a preferred embodiment of the present invention.

The specimens 104, along with the covers 106 and indicia 116/118, may be transferred to the film strip 102 using any suitable manual or automated method. For example, FIG. 2 illustrates a preferred embodiment of an automated biological specimen film assembler 200 that may be used to manufacture the specimen film 100 illustrated in FIG. 1. The assembler 200 generally comprises a film manipulator 202 configured for advancing the film strip 102 along a specified and fixed path. In particular, the film manipulator 202 comprises a film advancing device 204, a dispensing reel holder 206, a take-up reel holder 208, and a sample counter 210.

Figure 3:
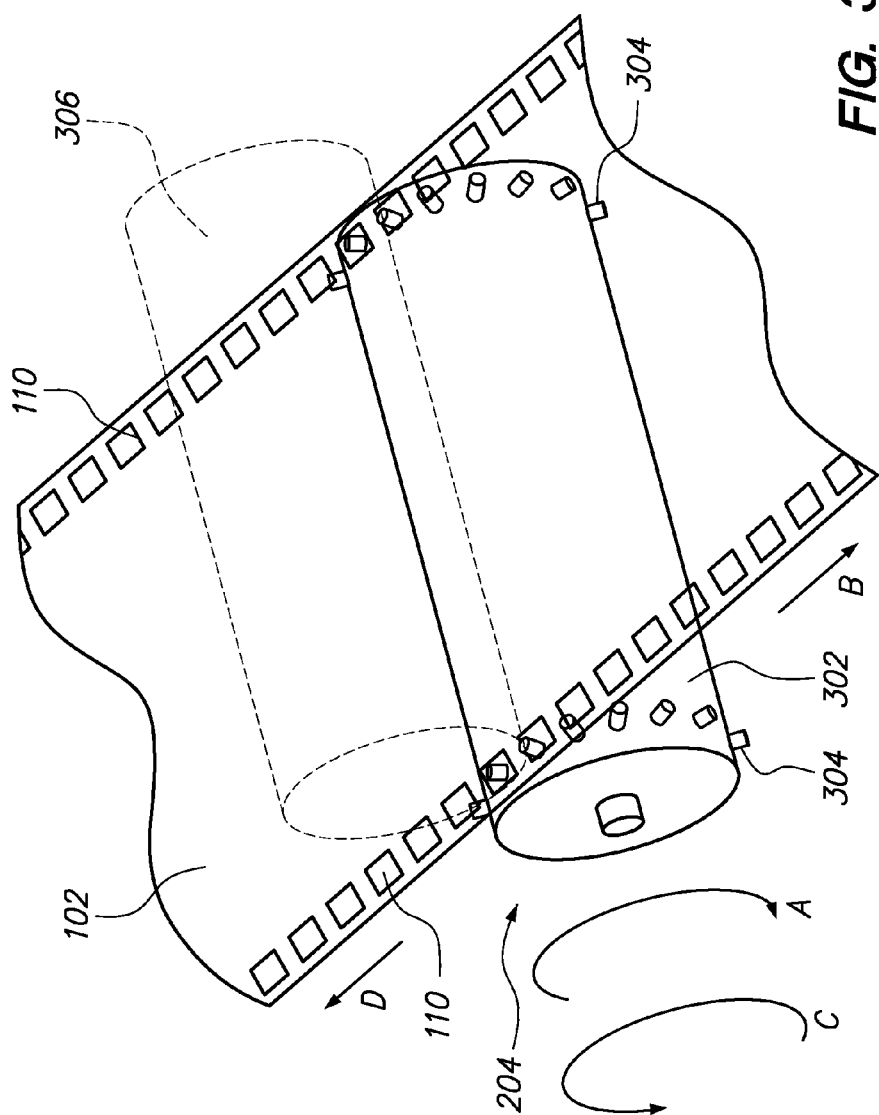
FIG. 3 is a perspective view of a film advancing device used in the film assembler of FIG. 2, the image processor of FIG. 6, or the review station of FIG. 7.

As shown in FIG. 3, the film advancing device 204 comprises a motorized sprocket 302 with cogs 304 spaced to engage the advancers 110 on the film strip 102. A spring loaded roller 306 presses the film 100 against the sprocket 302 to provide tension to keep the film 100 from bunching up or slipping off the sprocket 302. Rotation of the sprocket 302 in a clockwise direction (shown as arrow A) advances the film strip 102 in the forward direction (shown as arrow B), and rotation of the sprocket 302 in a counterclockwise direction (shown as arrow C) advances the film 102 in the reverse direction (shown as arrow D). The film advancing device 204 is configured to be locked in order to fix the position of the film strip 102.

The dispensing reel holder 206 is a solid arm configured to hold a reel of unused film 212 (i.e., film that comprises the film strip 102, with advancers 110, counter marks 112, and preprinted fiducial marks 114, but no specimens 104). The take-up reel holder 208 is a similar solid arm configured to hold and rotate a reel 214 for collection of the assembled film 100. The dispensing reel holder 206 and take-up reel holders 208 both have pulleys (not shown) that are engaged with a drive belt system (not shown), so that the reels 212/214 can be rotated in both clockwise and counterclockwise directions in coordination with the rotation of the sprocket 302. In this manner, coordinated rotation of the film reels 212/214 by the reel holders 206/208 and movement of the film strip 102 by the sprocket 302 moves the film strip 102 from the dispensing reel 212 to the take-up reel 214.

The sample counter 210 is configured to engage each counter mark 112 as the film strip 102 passes by. In this way, the sample counter 210 counts the number of frames 108 on the film strip 102, so that each specimen 106 located on the reel 214 can be subsequently designated with a count number and identified as such.

Figure 4:
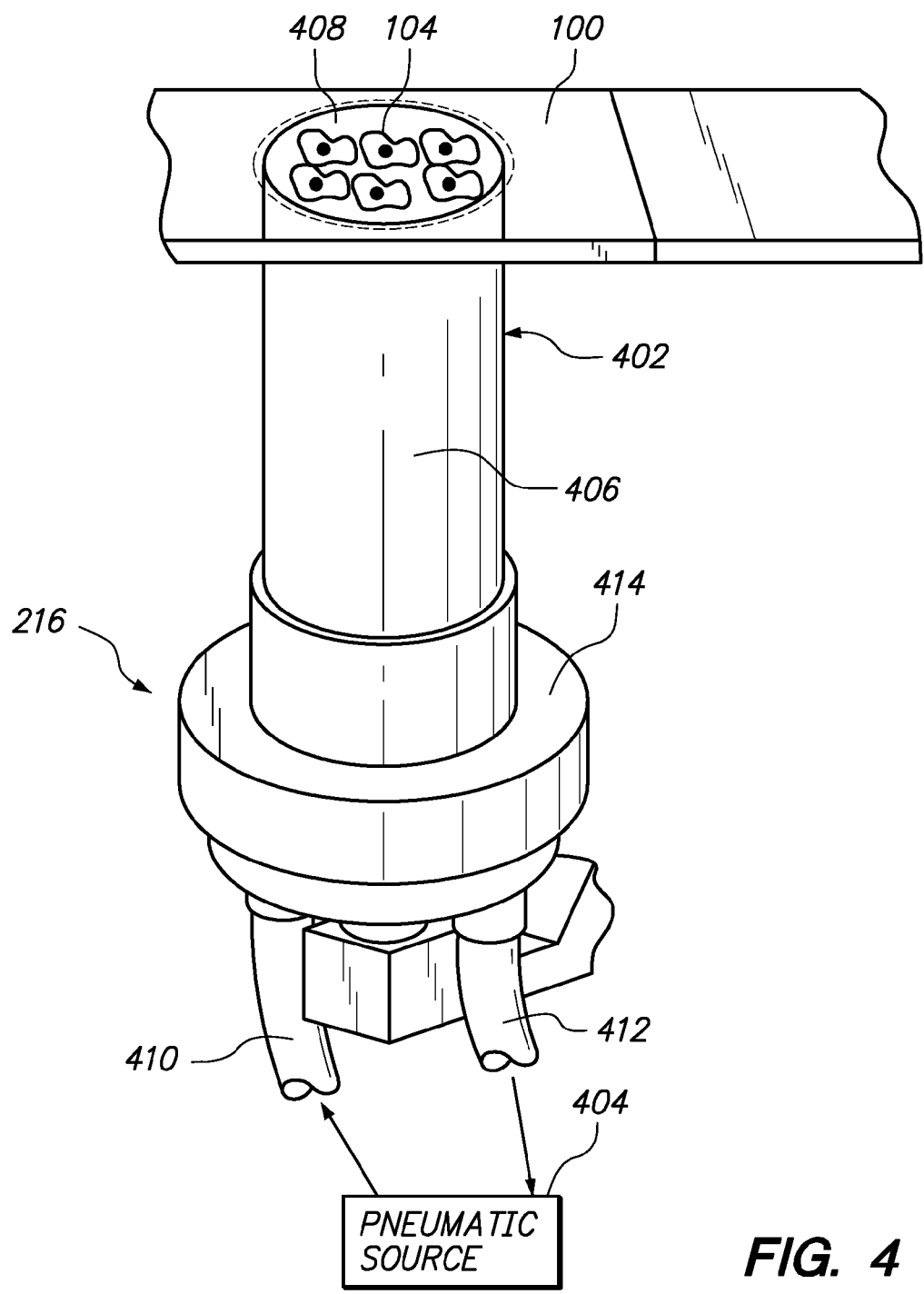
FIG. 4 is a perspective view of a biological specimen transfer device used in the film assembler of FIG. 2.

The specimen assembler 200 further comprises a transfer device 216 configured for transferring the biological specimens 104 onto the unused film. The transfer device 216 takes the form of an automated device that uses a transfer filter 402 and a pneumatic source 404 as its operative components, as shown in FIG. 4. The transfer filter 402 comprises a hollow cylinder 406 and a membrane 408 mounted to one end of the cylinder 406. The membrane 408 has pores (not shown) sized to keep the biological specimens 104 of interest, in this case, cervical cells, from passing through the membrane 408. The pneumatic source 404 is configured to exert positive pressure on the transfer filter 402 via a positive pressure hose 410 connected to the filter 402. The pneumatic source 404 is also configured to exert negative pressure on the transfer filter 402 via a negative pressure hose 412 connected to the filter 402. The hoses are connected to a cap 414 which seals the other end of the cylinder 406.

The specimen transfer device 216 further comprises vial handlers (not shown) and filter handlers (not shown) for manipulating sample vials (not shown) and transfer filters 402. The sample vials typically contain biological specimens 104 suspended in a liquid. The specimens 104 may be collected and dispersed into a liquid preservative or they may naturally exist in a collected biological liquid. Dispersion in liquid preservatives containing methanol, such as PreservCyt™ solution, breaks up mucus and lyses red blood cells and inflammatory cells, without affecting the cells of interest. The sample vials have identifying bar code characters printed thereon to identify the source of the biological specimens 104 in the vials. The transfer device 216 also comprises an optical character reader 218 configured to the read bar code characters as the biological specimens 104 are processed.

Further details describing the transfer device 216 and similar devices are further disclosed in U.S. Pat. Nos. 6,572,824, 6,618,190, 5,772,818, 5,364,597, and 5,143,627, which are expressly incorporated herein by reference.

The specimen assembler 200 further comprises a laminating device 220 configured to permanently bond affixation covers 106 onto the narrow film strip 102, and a printer 222 configured to print the indicia 116/118 onto the narrow film strip 102. The specimen assembler 200 further comprises an assembler controller 224 that is electrically connected to and coordinates the actions of the various components of the assembler 200.

In operation, the dispensing reel 212 of unused film is manually loaded onto the dispensing reel holder 206 and threaded onto the sprocket 302 in the film advancing device 204 and into the take-up reel 214 mounted on the take-up reel holder 208. This step is much like loading a film projector. The assembler controller 224 then directs the film advancing device 204 to position a specimen frame 108 of the film 100 in proximity to the filter 402 and locks it in place. The sample counter 210 interacts with the counter mark 112 on the film strip 102 and reports this interaction to the assembler controller 224.

The assembler controller 224 then directs the transfer device 216 to transfer a biological specimen 106 onto the locked specimen frame 108. In particular, the vial handler (not shown) positions the sample vial (not shown) containing a biological specimen 104 containing liquid in proximity to the transfer filter. The filter 402 is introduced into the vial and spun to disperse the biological specimen 104. Then, the membrane end of the filter 402 is dipped into the sample vial, and the pneumatic source 404 is operated to exert negative pressure on the filter 402. As a result, a predetermined amount of the liquid is withdrawn through the membrane 408 and into the filter 402, thereby collecting the biological specimen 104 on the membrane 408. Debris, such as lysed blood cells and dispersed mucus, which flow through the pores of the membrane, are not collected on the membrane and are greatly reduced by the combined method of dispersion and filtering.

Then, the biological specimen 104 is transferred from the filter 402 to the film strip 102 by briefly touching the membrane 408 to the film strip 102 at approximately the center of the specimen frame 108. The natural adhesion properties of the biological specimen 104 and the electrochemical charge of the film strip 102 are responsible for the transfer of the biological specimen 104 from the transfer filter to the film strip 102. The pneumatic source 404 is again operated to exert positive pressure on the filter 402 to facilitate transfer of the biological specimens 104 by forcing the biological specimens 104 off of the membrane 408 and onto the film strip 102.

During or after the specimen transfer process, the assembler controller 224 directs the optical character reader 218 to read the identifying bar code information from the vial and transmit it to the film assembler controller 224. The controller 224 then directs the printer 222 to print the indicia 116/118, based on information from the optical character reader 218 and the sample counter 210, in proximity to the biological specimen 104.

After the biological specimen 104 is transferred to the film strip 102, the controller 224 directs the film advancing device 204 to advance the film 100 to prepare the frame 108 with the newly transferred biological specimen 104 for lamination of the affixation cover 106 by the laminating device 220. Optionally, the biological specimen can be fixed and/or stained before application of the cover 106.

Advancing the film 100 also positions the next frame 108 on the unused film for transfer of the next biological specimen 104. The sample counter 210 counts the counter mark 112 and sends this information to the controller 224. This process is repeated until a specimen film 100 of the desired length is formed. The processed specimen film 100 is wound around the take-up reel 214 mounted on the take-up reel holder 208 to facilitate handling. Once the assembler 200 has finished preparing the biological specimen film 100 and winding it around the take-up reel 214, the dispensing reel 212 and take-up reel 214 are removed from the assembler 200 and loaded into a rewinder (not shown). The rewinder moves the film 100 from the take-up reel 214 to the dispensing reel 212 to return the film 100 to its initiate configuration and sequence of frames 108. Alternatively, the analyzer 500 may use software to track the sequence of frames 108 on a film 100.

In the illustrated embodiment, a reel of specimen film 100 may contain 200 or more biological specimens 104, although a lesser number of specimens 104 can be provided. Alternatively, the biological specimen film 100 may be fabricated manually, although an automated fabrication method, as just described, provides a convenient means for transferring the biological specimens 104 to the film strip 102 at a much higher rate.

Figure 8:
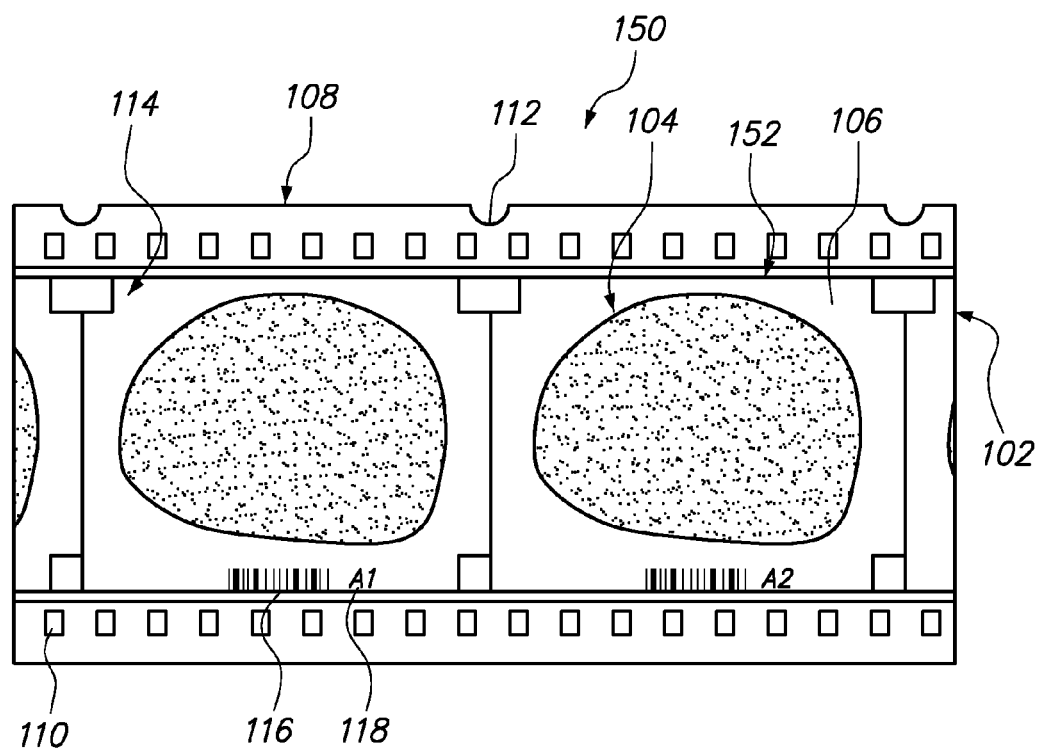
FIG. 8 is a top view of another biological specimen film constructed in accordance with a preferred embodiment of the present invention.

Although the film 100 described above comprises specimens 104 that are affixed directly to the film strip 102, specimens may alternatively be disposed on the film strip 102 in other manners, such as through the use of slides. For example, FIG. 8 illustrates a biological specimen film 150 that is similar to the previously described film 100, with the exception that it comprises a plurality of slides 152 on which the biological specimens 104 are disposed. The slides 152, along with the specimens 104 and associated affixation covers 106, are then suitably affixed to the film strip 102 (e.g., by bonding with an adhesive), with each slide 152 occupying a biological specimen frame 108. In this embodiment, the fiducial marks 114 and machine readable and human readable indicia 116/118 are printed on the slides 150 adjacent the respective specimens 104.

The specimen film 150 depicted in FIG. 8 may be assembled by adhering the prepared slides 152 (i.e., slides 152 with biological specimens 104, covers 106, and indicia 116/118 already transferred thereon using known techniques) to the film strip 102. Alternatively, blank slides 820, featuring only fiducial marks 114 may be adhered to the film strip 102. Then the previously described specimen film assembler 200 can be used to transfer the biological specimens 104 to the blank slides 152 on the film strip 102 in the same manner as the biological specimens 104 were directly applied to the film strip 102 as previously described.

Figure 5:
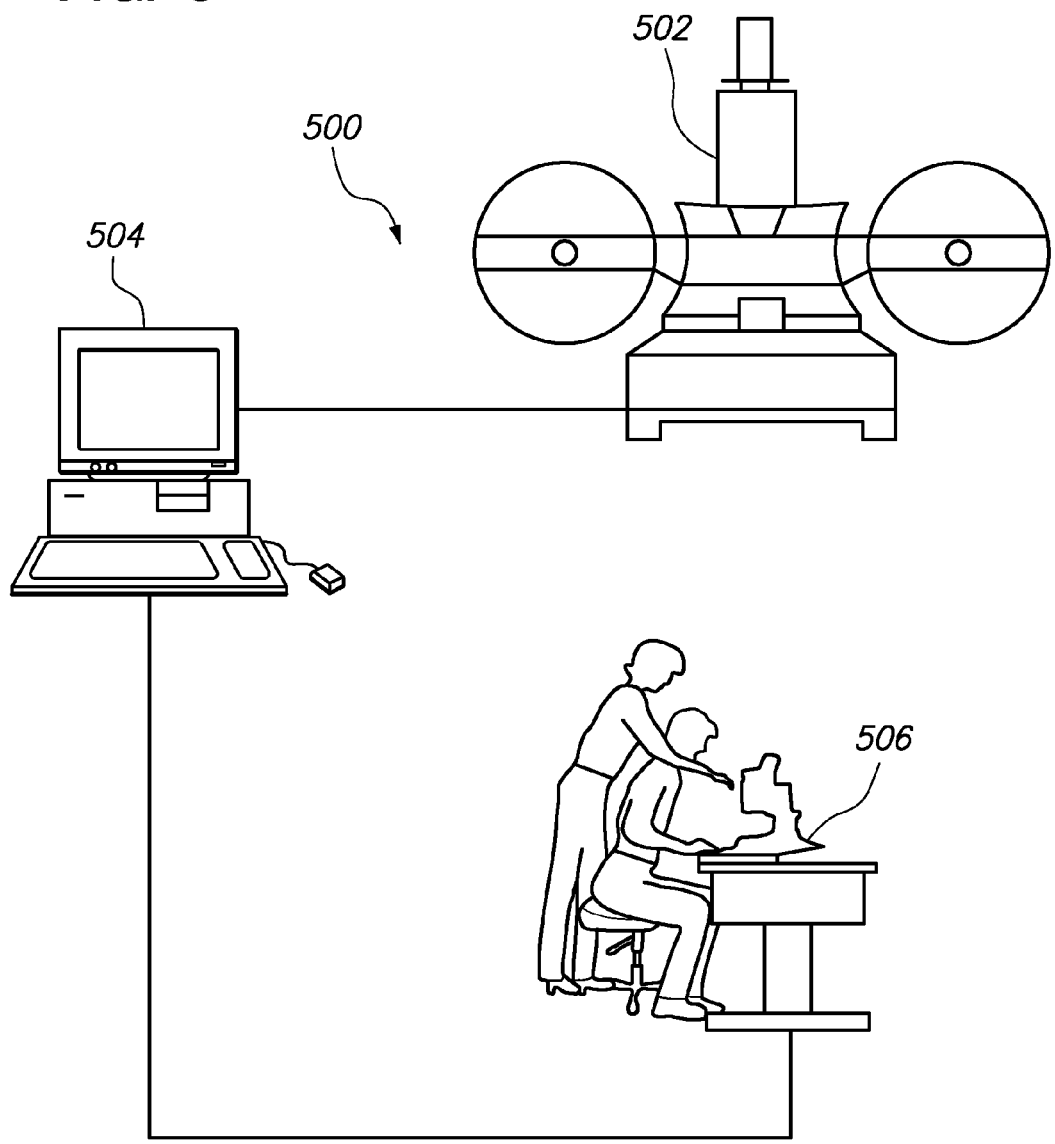
FIG. 5 is a schematic diagram of a biological specimen film analyzer constructed in accordance with a preferred embodiment of the present invention.

Referring to FIG. 5, a preferred embodiment of a biological specimen analyzer 500 will now be described. The analyzer 500 comprises an image processor 502, a review station 506, and a computer server 504. The image processor 502 is configured to acquire images of biological specimens 104 and identify areas of interest for later review. The review station 506 is configured to allow a human operator to review the areas of interest previously identified by the image processor 502. The server 504 is in communication with both the image processor 502 and the review station 506, and coordinates the operations of, and data flow between, the image processor 502 and the review station 506.

Figure 6:
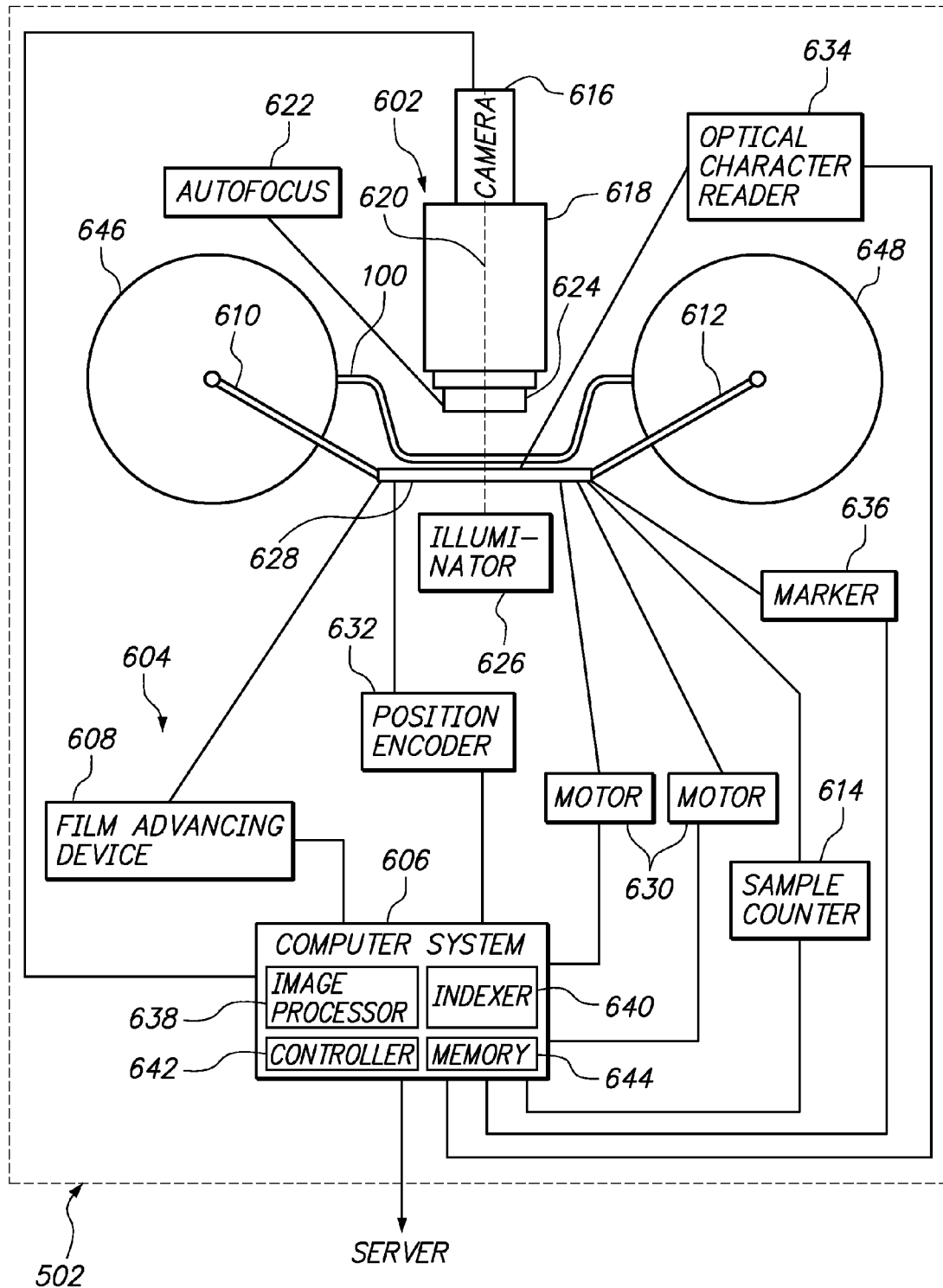
FIG. 6 is a schematic diagram of an image processor used in the film analyzer of FIG. 5.

Referring to FIG. 6, the image processor 502 will now be described in greater detail. The image processor 502 includes a scanning device 602 for acquiring magnified images of the biological specimens 104 carried by the specimen film 100 (or alternatively, the film 150), a film manipulator 604 for mechanically manipulating a strip of film movable relative thereto, and a computer system 606 for analyzing the magnified images and identifying the locations of objects of interest within the biological specimens 104.

Like the film manipulator 202 described previously with respect to the film assembler 100, the film manipulator 604 comprises a film advancing device 608, a dispensing reel holder 610, a take-up reel holder 612, and a sample counter 614, which operate together to place a designated biological specimen 104 in the path of the scanning device 602. These components are similar to the same-named components previously described, and will thus, not be described in further detail.

The scanning device 602 comprises an electronic camera 616, such as a CCD camera, and a microscope 618. The microscope 618 is preferably an automated microscope having an optical path 620. The automated microscope 618 includes features to provide fast, precise imaging of a region of the specimen frame 108 positioned in the optical path 620 of the microscope 618, such as an autofocusing mechanism 622. The scanning device 602 also comprises one or more objective lens systems 624 and an illuminator 626, which provides illumination for the biological specimen 104 deposited on the biological specimen film 100 and generally illuminates the biological specimen film 100. The electronic camera 616 is positioned in the optical path 620 of the microscope 618, so as to capture an electronic image of the region of the specimen frame 108 being viewed. In one embodiment; the field of view of the camera 616 is 640 pixels in width by 480 pixels in length. Each pixel is on the order of about 0.74 microns. These electronic images are then sent to the computer system 606 as electronic signals, so that the computer system 606 can perform an analysis of the cells appearing in the imaged region, as well be described in further detail below.

The scanning device 602 further comprises a motorized stage 628 on which the film manipulator 604, along with a designated biological specimen 104, is mounted. The scanning device 702 also comprises x-y motors 630 configured to move the stage 628, and thus the film manipulator 604, in the x-y plane perpendicular to the optical path 620. The computer system 606 provides precise controlled movements of the stage 628, and the selected specimen frame 108 mounted thereon relative to the optical path 620 and viewing area of the microscope 618.

The scanning device 602 also comprises a position encoder 632 for detecting the precise location of the stage 628 and the specimen frame 108 mounted thereon, and producing to the computer system 606 pulses representative of the movement or location of the stage 628. As known in the art, these pulses may be decoded by the computer system 606 in order to identify the location of the specimen frame 108 in an imaging station coordinate system.

The scanning device 602 further comprises an optical character reader 634 positioned to view the sample identification mark 116, once the specimen frame 108 has been mounted on the stage 628. In this embodiment, the scanning device 602 also comprises a marking device 636 that automatically places a dot, a mark, or other visible sign in the areas of interest within the specimen where potentially abnormal cells may be located.

The computer system 606 comprises (1) an image processor 638 that is configured to obtain objects of interest from the image data acquired from the camera 616; (2) an indexer 640 configured to establish a coordinate system for each frame 108, so that the x-y coordinates of the frame 108 during the review process can be correlated to the x-y coordinates of the frame 108 obtained during the imaging process; (3) a controller 642 that is configured to coordinate movement of all moving parts in the image processor 502; and (4) a memory 644 configured for storing all the information received from the image processor 502.

The image processor 638 performs the necessary analysis in order to determine whether malignant or pre-malignant cells are contained in the biological specimen 104 based upon their appearance. The image processor 638 may rely on feature extraction algorithms, which attempt to select and to measure some feature within the image, e.g., the shape or the size of the cell nucleus, or the density of cells within the region. For instance, an unusually large sized nucleus may indicate cell abnormality. Based on pre-programmed criteria, the image processor 638 identifies objects of interest, and in particular, those regions within the biological specimen 104 most likely to contain certain features of interest, such as cell abnormalities. Typically, the image processor 502 identifies between about 10 to about 30 areas of interest within the biological specimen 104, although the number of areas of interest may vary from 0 to 100 or more. The indexer 640 establishes an x-y coordinate system based on the fiducial marks 114 in each frame 108. Establishing a coordinate system is also known as indexing. The indexer 640 determines the location of the first fiducial mark 114 and measures the respective x and y distances that separate the second and third fiducial marks 114 from the first. The indexer 640 uses this information to establish an x-y coordinate system. Information about this x-y coordinate system is stored in the memory 644 and transmitted to the server 504 to correlate the x-y coordinates of the frame 108 during the review process to the x-y coordinates of the frame 108 obtained during the imaging process. Further details regarding the indexer 640 are described in U.S. patent application Ser. No. 09/430,198, entitled "Apparatus and Methods for Verifying the Location of Areas of Interest Within a Sample in an Imaging System," which is expressly incorporated herein by reference.

The controller 642 coordinates the movement of the elements of the image processor 502, specifically, the frame advancing device 608, the reel holders 610/612, and the motors 630. During a scan, the controller 642 directs the x-y motors 630 to move the film manipulator 604 in such a way that the designated specimen frame 108 of the specimen film 100 is positioned in the optical path 620 of the microscope 618. As the stage 628 is moved by the x-y motors 630 in response to the signals from the controller 642, the image viewed by the objective lens system 624 of the microscope 618 also is moved, so as to view another portion of specimen frame 108. Thus, the image processor 502 scans the biological specimen 104 by moving the film manipulator 604, and therefore the field of view of the microscope 618, across the entire biological specimen 104. The number of regions scanned per biological specimen 104 can be around 2,200 or more.

Further details regarding the scanning device 602 are described in U.S. patent application Ser. Nos. 09/430,198, entitled "Apparatus and Methods for Verifying the Location of Areas of Interest Within a Sample in an Imaging System," and U.S. Provisional Patent Application Ser. No. 60/478,431, entitled "Method and System of Organizing Multiple Objects of Interest In Field of Interest," which are both expressly incorporated herein by reference.

Figure 7:
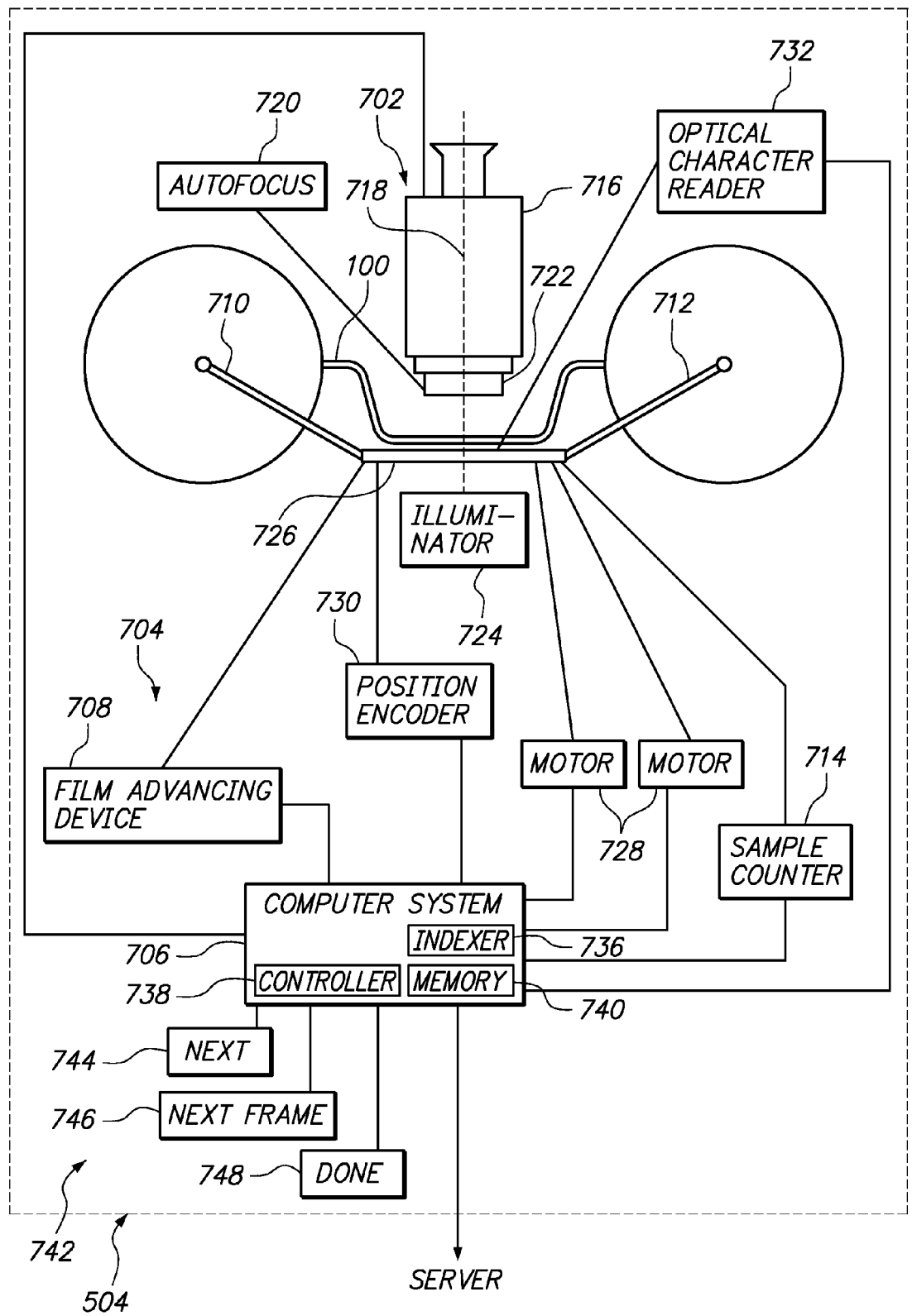
FIG. 7 is a schematic diagram of a review station used in the film analyzer of FIG. 5.

Referring to FIG. 7, the review station 506 will now be described in greater detail. The review station 506 includes a scanning device 702 for presenting magnified images of the biological specimens 104 carried by the specimen film 100 for review by a human operator (not shown), a film manipulator 704 for mechanically manipulating a strip of film movable relative thereto, and a computer system 706 for indexing the frames 108 of the specimen film 100 and providing locations of objects of interest within the biological specimens 104.

Like the film manipulator 202 described previously with respect to the film assembler 100, the film manipulator 704 comprises a film advancing device 708, a dispensing reel holder 710, a take-up reel holder 712, and a sample counter 714, which operate together to place a designated biological specimen 104 in the path of the scanning device 702. These components are similar to the same-name components previously described, and will thus, not be described in further detail.

Like the scanning device 602 described previously with respect to the image processor 502, the scanning device 702 comprises a microscope 716 having an optical path 718, an autofocusing mechanism 720, one or more objective lens systems 722, an illuminator 724, a motorized stage 726, x-y motors 728, a position encoder 730, and an optical character reader 732. These components are similar to the same-name components previously described, and will thus, not be described in further detail. The scanning device 702 further comprises an ocular lens system 734 configured to allow a human operator to review magnified images of the biological specimens 104 carried by the specimen film 100, as well be described in further detail below.

The computer system 706 comprises an indexer 736, a controller 738, and a memory 740. These components are similar to the same-named components previously described, and will thus, not be described in further detail. The computer system further comprises semi-automatic controls 742 configured to allow a human operator to direct the scanning device 702 to position the next area of interest in the optical path 718 of the microscope 716 by pressing a NEXT button 744. The semi-automatic controls 742 are also configured to allow a human operator to direct the film manipulator 704 to advance to the next frame 108 of the film 100 by pressing a NEXT FRAME button 746 and to end the scan by pressing a DONE button 748.

Further details regarding the scanning device 702 and computer system 706 are described in U.S. patent application Ser. No. 09/430,198, and U.S. Provisional Patent Application Ser. No. 60/478,431, which have previously been incorporated herein by reference.

In operation generally, the image processor 502 performs an initial viewing and screening of all of the specimen frames 108 of the specimen film 100 on which the biological specimens 104 are disposed, in order to make a preliminary assessment of the biological specimens 104. The image processor 502 identifies for subsequent viewing by a cytotechnologist or pathologist the locations of those areas of interest on each specimen frame 108 that potentially are most relevant. This region identifying information is linked with biological specimen identifying information read from the sample identification mark 116 and stored in the computer system 606 or the computer server 504. Once all of the specimen frames 108 of the specimen film 100 have been scanned by the scanning device 602 in the image processor 502, the biological specimen film is transferred to the review station 506 for subsequent viewing.

More specifically, the specimen film 100 is first loaded into the image processor 502, by mounting a dispensing reel 646 around which the specimen film 100 is initially wound onto the dispensing reel holder 610. Then, the film 100 is fed through the film advancing device 608 and into a take-up reel 648 mounted on the take-up reel holder 612. In response to appropriate commands from the internal computer system 606, the film advancing device 608 advances the specimen film 100 and positions the first specimen frame 108 into and within the optical path 620 of the microscope 618. Then, the film advancing device 608 fixes the position of the sprocket 302 and, thus, of the specimen frame 108 in the stage 628. The x-y motors 630 are then ready to move the film manipulator 604 and the specimen frame 108 fixed therein in the x-y plane for scanning.

The optical character reader 634 reads the machine readable indicia 116 in the specimen frame 108, and sends the identifying information to be stored in the memory 644. The sample counter 614 also interacts with the counter marks 112 to count the number of biological specimens 104 that have passed through the image processor 502. This information is also stored in the memory 644 and provides an independent system for identifying the specimen frames 108 on a specimen film 100.

The indexer 640 then indexes the frame 108, using the fiducial marks 114 in the frame 108 to establish a coordinate system that is stored in the memory 644. Then, the image processor 502 scans the entire biological specimen 104 in the specimen frame 108, typically containing tens of thousands of cells, in order to determine the potentially most relevant areas of interest within the biological specimen 104, such as cells with excessively large and/or dark nuclei.

Once the areas of interest have been identified, the computer system 606 ranks the identified regions based on the degree to which each region has characteristics more likely found in a typical premalignant or malignant cell than in a typical benign cell. The computer system 606 then assigns to each identified region a coordinate value in the coordinate system established by the indexer 640, thereby determining the relative location of each area with respect to the first, second, and third fiducial marks 114. The computer system 606 then stores in memory 644 a file containing the coordinate values of each area of interest and the identifying information for the frame. The image processor 502 also communicates this data with the server 504. The marking device 636 then places a visible sign on the specimen film 100 at the locations of each identified area of interest to aid the pathologist in identifying the potentially malignant cells at the review station 506.

After the entire specimen frame 108 has been scanned by the image processor 502, the controller 642 sends an appropriate signal to the film advancing device 608 to advance the film 100 by one frame 116. Then, the next specimen frame 108 is scanned by the image processor 502. The scanned frames 116 of the film 100 are collected on the take-up reel 648 mounted on the take-up reel holder 612 for easy handling. Once image processor 502 has scanned all of the specimen frames 108 on the biological specimen film 100 and wound the film 100 around the take-up reel 648, the film is removed from the image processor 502 and rewound in the same manner that the film 100 was removed from the assembler 200 and rewound.

In the review station 506, the once-scanned specimen film 100 is submitted for review by a human operator, who may be a cytotechnologist doing another preliminary screen for a pathologist, or may be a pathologist doing a final screen. Either way, the image processor 502 has electronically limited for the human operator the regions within each specimen frame 108 that require inspection by the human operator.

The rewound specimen film 100 is loaded into the review station 506 in the same manner that the specimen film 100 was loaded into the image processor 502. The advancing device 708 then advances the film 100 to the first specimen frame 108. Then, the optical character reader 732 reads the machine readable indicia 116 in the specimen frame 108, and sends the identifying information to the computer system 706. The sample counter 714 also interacts with the counter marks 112 to count the number of biological specimens 104 that have passed through the review station 506. This information is also sent to the computer system 706 and provides an independent basis for identifying the specimen frames 108 on a specimen film 100.

The indexer 736 then automatically correlates the x-y coordinate system in the review station to the x-y coordinate system established by the indexer 640 in the image processor 502. The server 504 provides the x-y coordinates that were assigned to the areas of interest for that specimen frame 108 by the image processor 502. These x-y coordinates, which were acquired relative to the x-y coordinate system of the image processor 502, are transformed by the computer system 706 into the x-y coordinate system of the review station 506. Thus, it is ensured that the x-y coordinates of the frame 108 during the reviewing process are correlated to the x-y coordinates of the frame 108 during the imaging process. Indexing the frame 108 in this manner assures that the review station will allow a human operator to scan the previously identified areas of interest.

The human operator directs the scanning device 702 to go to the first assigned coordinate by hitting the NEXT button 744. This directs the controller 742 to cause the motors 730 to move the stage 728 and the biological specimen 104 mounted thereon to the x-y coordinates of the first area of interest. After examining the area corresponding to the first assigned coordinate, the operator hits the NEXT button 744 again, which directs the scanning device 702 to go to the coordinates of the next area of interest. In this manner, the human operator goes through the entire range of locations that have been selected for review by the image processor 502. If the human operator is a cytotechnologist, he may further identify certain regions if the operator thinks that a cell or a cluster of cells is of interest.

After the human operator has reviewed the last area of interest, the operator hits the NEXT FRAME button 746, causing the film advancing device 708 to bring the next specimen frame 108 into the optical path 718 of the microscope 716. The above-described review process is repeated with each specimen frame 108 until all of the frames 116 of the specimen film 100 have been reviewed. After all the frames 116 have been reviewed, the operator hits the DONE button 748, terminating the review. The film 100 is then removed from the review station 506 and rewound as previously described.

If the human operator is a cytotechnologist, the specimen film 100 is then submitted for review by a pathologist, who makes the final determination as to whether or not the areas of interest contain malignant cells. Alternatively, the human operator in the review station may be the pathologist himself, who reviews each of the areas corresponding to the coordinates stored in the server 504 by the image processor 502, and makes a final determination for each area.

In one embodiment, a plurality of image processors 502 and review stations 506 may be in use in coordination via a common server 506. As a specimen film 100 is transferred from one image processor 502 to another, or from one image processor 502 to one of the plurality of review stations 506, information regarding the locations of areas of interest on each specimen frame 108 of the specimen film 100 may be stored and shared among the plurality of image processors 502 and review stations 506, so that any of the equipment can be used interchangeably with a high degree of confidence that the proper regions are being reviewed by the pathologist.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A biological specimen film, comprising:
   a continuous strip of flexible film topologically divided into a plurality of discrete specimen frames;
   film advancers located along the film strip;
   a plurality of discrete biological specimens disposed on the film strip, each discrete specimen frame including a discrete biological specimen;
   a plurality of discrete affixation covers disposed on the film strip over respective discrete biological specimens; and
   a plurality of fiducial marks on the film strip, wherein at least one fiducial mark is located inside of each discrete specimen frame.

2. The film of claim 1, wherein the discrete biological specimens are affixed directly onto the film strip.

3. A biological specimen film, comprising:
   a continuous strip of flexible film topologically divided into a plurality of discrete specimen frames;
   film advancers located along the film strip;
   a plurality of discrete biological specimens disposed on the film strip, each discrete specimen frame including a discrete biological specimen;
   a plurality of fiducial marks on the film strip, each discrete specimen frame including a fiducial mark; and
   a plurality of slides disposed on the film strip, wherein a discrete biological specimen is affixed to each slide, each slide occupying a discrete specimen frame.

4. The film of claim 1, at least one fiducial mark being located on the film strip adjacent each discrete biological specimen.

5. The film of claim 1, further comprising a plurality of identifiers located on the film strip, each discrete specimen frame being associated with an identifier, each identifier containing unique information related to a corresponding discrete biological specimen.

6. The film of claim 1, further comprising a counter mark located between adjacent discrete specimen frames.

7. The film of claim 1, wherein the plurality of discrete biological specimens comprises at least 200 discrete biological specimens.

8. The film of claim 1, wherein the plurality of discrete biological specimens are applied to the film as a single column.

9. The film of claim 1, wherein the plurality of discrete biological specimens are discrete cytological specimens.

10. A biological specimen film reel, comprising:
    a continuous strip of film topologically divided into a plurality of discrete specimen frames;
    a plurality of discrete biological specimens disposed on the film strip, each discrete specimen frame including a discrete biological specimen;
    a plurality of discrete affixation covers disposed on the film strip over respective discrete biological specimens;
    a plurality of fiducial marks on the film strip, wherein at least one fiducial mark is located inside of each discrete specimen frame; and
    a reel carrying the film strip.

11. The film reel of claim 10, wherein the plurality of discrete biological specimens are affixed directly onto the film strip.

12. The film reel of claim 10, at least one fiducial mark being located on the film strip adjacent each discrete biological specimen.

13. The film reel of claim 10, further comprising a plurality of identifiers located on the film strip, each discrete specimen frame being associated with an identifier, each identifier containing unique information related to a corresponding discrete biological specimen.

14. The film reel of claim 10, further comprising a counter mark located between adjacent discrete specimen frames.

15. The film reel of claim 10, further comprising a plurality of film advancers affixed to the film strip.

16. The film reel of claim 10, wherein the plurality of discrete biological specimens comprises at least 200 discrete biological specimens.

17. The film reel of claim 10, wherein the plurality of discrete biological specimens are applied to the film as a single column.

18. The film reel of claim 10, wherein the plurality of discrete biological specimens are discrete cytological specimens.

19. A method of preparing biological specimens, comprising:
    providing a continuous, flexible film strip that is topologically divided into a plurality of discrete specimen frames and that includes a plurality of fiducial marks, wherein a fiducial mark is located inside of each discrete specimen frame;
    applying a plurality of discrete biological specimens along the film strip, each discrete specimen frame including a discrete biological specimen; and
    applying a plurality of discrete covers to the film strip over respective discrete biological specimens.

20. The method of claim 19, the plurality of discrete biological specimens being affixed directly onto the film strip.

21. A method of preparing biological specimens, comprising
    providing a continuous, flexible film strip that is topologically divided into a plurality of discrete specimen frames and that includes a plurality of fiducial marks, each discrete specimen frame including a fiducial mark;
    applying a plurality of discrete biological specimens along the film strip, each discrete specimen frame including a discrete biological specimen by affixing the plurality of discrete biological specimens onto a plurality of slides and applying the plurality of slides onto the film strip, each slide occupying a discrete specimen frame.

22. The method of claim 19, further comprising winding the film strip around a reel.

23. The method of claim 19, at least one fiducial marks being located on film strip adjacent each discrete biological specimen.

24. The method of claim 19, further comprising applying identifiers along the length of the film strip, each discrete specimen frame being associated with an identifier, each identifier containing unique information related to a corresponding discrete biological specimen.

25. The method of claim 19, wherein the film strip has counter marks between adjacent discrete specimen frames.

26. The method of claim 19, wherein the film strip has a plurality of film advancers along its length.

27. The method of claim 19, wherein the plurality of discrete biological specimens are automatically applied to the film.

28. The film of claim 1, wherein the plurality of fiducial marks are arranged on the film strip in a non-colinear manner.

29. The film of claim 1, wherein each frame includes fiducial marks arranged in a non-colinear manner.

30. The film of claim 1, wherein the plurality of fiducial marks are in the same positions within each frame.

* * * * *